United States Patent
Godfrey (10) Patent No.: US 7,151,456 B2
(45) Date of Patent: Dec. 19, 2006

(54) MEDICAMENT DISPENSER

(75) Inventor: James William Godfrey, Ware (GB)

(73) Assignee: Glaxo Group Limited, Greenford (GB)

( * ) Notice: Subject to any disclaimer, the term of this patent is extended or adjusted under 35 U.S.C. 154(b) by 7 days.

(21) Appl. No.: 10/204,843

(22) PCT Filed: Feb. 21, 2001

(86) PCT No.: PCT/EP01/01941

§ 371 (c)(1),
(2), (4) Date: Aug. 23, 2002

(87) PCT Pub. No.: WO01/62322

PCT Pub. Date: Aug. 30, 2001

(65) Prior Publication Data

US 2003/0011476 A1    Jan. 16, 2003

(30) Foreign Application Priority Data

Feb. 26, 2000 (GB) .................................. 0004456.0

(51) Int. Cl.
*G08B 23/00* (2006.01)
(52) U.S. Cl. .............................. 340/573.1; 128/200.14; 340/572.8; 604/403; 705/3
(58) Field of Classification Search ............ 340/573.1, 340/572.7, 693.5, 540, 505, 10.1, 572.8; 128/203.12, 200.14; 604/890.1, 48, 57, 58, 604/403, 404, 407, 416; 705/2, 3, 28
See application file for complete search history.

(56) References Cited

U.S. PATENT DOCUMENTS

| | | | |
|---|---|---|---|
| 4,679,426 A | 7/1987 | Fuller et al. | |
| 4,724,427 A | 2/1988 | Carroll et al. | |
| 4,817,822 A | 4/1989 | Rand et al. | |
| 4,940,966 A | 7/1990 | Pettigrew et al. | |
| 5,025,246 A | 6/1991 | Schenkel et al. | |
| 5,321,619 A | 6/1994 | Matsuda et al. | |
| 5,347,274 A | 9/1994 | Hassett | |
| 5,363,842 A | 11/1994 | Mishelevich et al. | |
| 5,368,948 A | 11/1994 | Davies et al. | |
| 5,381,137 A | 1/1995 | Ghaem et al. | |
| 5,448,110 A | 9/1995 | Tuttle et al. | |
| 5,469,363 A | 11/1995 | Saliga et al. | |
| 5,491,473 A | 2/1996 | Gilbert | |
| 5,505,195 A | 4/1996 | Sallis et al. | |
| 5,507,277 A | 4/1996 | Rubsamen et al. | |
| 5,508,203 A | 4/1996 | Fuller et al. | |
| 5,516,692 A | 5/1996 | Berndt | |
| 5,520,166 A | 5/1996 | Ritson et al. | |
| 5,528,221 A | 6/1996 | Jeuch et al. | |
| 5,541,604 A | 7/1996 | Meier et al. | |

(Continued)

FOREIGN PATENT DOCUMENTS

DE           19621179           11/1997

(Continued)

*Primary Examiner*—Thomas Mullen
(74) *Attorney, Agent, or Firm*—James P. Riek (57) ABSTRACT

A medicament dispenser comprising a housing; a medicament container; a dispensing mechanism for dispensing medicament from the medicament container; and a radiofrequency identifier connecting to the housing or the medicament container, in the form of a radiofrequency identification tag comprising: an antenna for transmitting or receiving radiofrequency energy originating from an external remote reader; and an integrated circuit chip connecting with the antenna. The dispensing mechanism may, for example, comprise a valve, with or without a metering chamber, for dispensing aerosol formulations of medicaments, or opening or peeling mechanisms for blister strips or packs for dispensing dry powder medicaments.

51 Claims, 7 Drawing Sheets

U.S. PATENT DOCUMENTS

| | | | |
|---|---|---|---|
| 5,549,101 A | 8/1996 | Trofast et al. | |
| 5,560,353 A | 10/1996 | Willemot et al. | |
| 5,582,795 A | 12/1996 | Nishina et al. | |
| 5,583,819 A | 12/1996 | Roesner et al. | |
| 5,587,578 A | 12/1996 | Serra | |
| 5,608,739 A | 3/1997 | Snodgrass et al. | |
| 5,629,981 A | 5/1997 | Nerlikar | |
| 5,682,143 A | 10/1997 | Brady et al. | |
| 5,706,801 A | 1/1998 | Remes et al. | |
| 5,755,218 A | 5/1998 | Ritson et al. | |
| 5,770,455 A | 6/1998 | Cargill et al. | |
| 5,771,657 A | 6/1998 | Rice et al. | |
| 5,774,875 A | 6/1998 | Medeiros et al. | |
| 5,777,303 A | 7/1998 | Berney | |
| 5,792,668 A | 8/1998 | Fuller et al. | |
| 5,796,602 A | 8/1998 | Wellan et al. | |
| 5,799,651 A | 9/1998 | Garby et al. | |
| 5,809,997 A | 9/1998 | Wolf | |
| 5,813,397 A | 9/1998 | Goodman et al. | |
| 5,821,524 A | 10/1998 | Horlbeck et al. | |
| 5,844,802 A | 12/1998 | Lepper et al. | |
| 5,874,214 A | 2/1999 | Nova et al. | |
| 5,874,896 A | 2/1999 | Lowe et al. | |
| 5,892,441 A | 4/1999 | Woolley et al. | |
| 5,898,370 A | 4/1999 | Reymond | |
| 5,920,054 A | 7/1999 | Uber, III | |
| 5,955,950 A | 9/1999 | Gallagher et al. | |
| 5,959,531 A | 9/1999 | Gallagher et al. | |
| 5,961,925 A | 10/1999 | Ruediger et al. | |
| 5,963,136 A * | 10/1999 | O'Brien | 340/573.1 |
| 5,972,156 A | 10/1999 | Brady et al. | |
| 5,981,166 A | 11/1999 | Mandecki et al. | |
| 5,986,562 A | 11/1999 | Nikolich et al. | |
| 6,002,344 A | 12/1999 | Bandy et al. | |
| 6,008,727 A | 12/1999 | Want et al. | |
| 6,017,496 A | 1/2000 | Nova et al. | |
| 6,018,299 A | 1/2000 | Eberhardt et al. | |
| 6,025,780 A | 2/2000 | Bowers et al. | |
| 6,032,666 A | 3/2000 | Davies et al. | |
| 6,040,773 A | 3/2000 | Vega et al. | |
| 6,040,774 A | 3/2000 | Schepps et al. | |
| 6,046,003 A | 4/2000 | Mandecki | |
| 6,049,278 A | 4/2000 | Guthrie et al. | |
| 6,078,845 A | 6/2000 | Friedman et al. | |
| 6,147,604 A | 11/2000 | Hugh et al. | |
| 6,148,815 A | 11/2000 | Wolf | |
| 6,202,642 B1 | 3/2001 | McKinnon et al. | |
| 6,259,654 B1 * | 7/2001 | de la Huerga | 368/10 |
| 6,294,999 B1 * | 9/2001 | Yarin et al. | 340/573.1 |
| 6,366,824 B1 | 4/2002 | Nair et al. | |
| 6,594,611 B1 | 7/2003 | Beffa | |
| 6,729,327 B1 | 5/2004 | McFarland | |
| 6,729,330 B1 | 5/2004 | Scarrott | |
| 6,839,604 B1 | 1/2005 | Godfrey | |
| 2002/0198618 A1 | 12/2002 | Madden et al. | |
| 2003/0064029 A1 | 4/2003 | Tarara et al. | |
| 2003/0079744 A1 | 5/2003 | Bonney et al. | |
| 2003/0183226 A1 | 10/2003 | Brand et al. | |
| 2003/0183697 A1 | 10/2003 | Porter | |
| 2004/0025871 A1 | 2/2004 | Davies | |
| 2004/0100415 A1 | 5/2004 | Veitch et al. | |

FOREIGN PATENT DOCUMENTS

| | | |
|---|---|---|
| DE | 19753619 | 5/1999 |
| DE | 19806049 | 8/1999 |
| DE | 19826568 | 12/1999 |
| DE | 29915334 | 1/2000 |
| EP | 645631 | 3/1995 |
| EP | 727752 | 8/1996 |
| EP | 786357 | 7/1997 |
| EP | 831410 | 3/1998 |
| EP | 0853288 | 7/1998 |
| EP | 859299 | 8/1998 |
| EP | 895087 | 2/1999 |
| EP | 908840 | 4/1999 |
| EP | 947952 | 10/1999 |
| EP | 0967568 | 12/1999 |
| FR | 2656446 | 6/1991 |
| FR | 2760209 | 9/1998 |
| GB | 2076259 | 9/1981 |
| GB | 2249001 | 4/1992 |
| GB | 2262452 | 6/1993 |
| GB | 2297225 | 7/1996 |
| GB | 2308947 | 7/1997 |
| GB | 2312595 | 10/1997 |
| GB | 2314418 | 12/1997 |
| GB | 2328281 | 2/1999 |
| JP | 08195697 | 7/1996 |
| JP | 10013295 | 1/1998 |
| JP | 10040329 | 2/1998 |
| JP | 10049620 | 2/1998 |
| JP | 10123147 | 5/1998 |
| JP | 11304812 | 11/1999 |
| JP | 11352243 | 12/1999 |
| WO | WO 92/12402 | 7/1992 |
| WO | WO 92/17231 | 10/1992 |
| WO | WO 94/07225 | 3/1994 |
| WO | 9522365 | 8/1995 |
| WO | WO 96/31790 | 10/1996 |
| WO | WO 97/04338 | 2/1997 |
| WO | WO 97/07443 | 2/1997 |
| WO | WO 97/10896 | 3/1997 |
| WO | WO 98/05088 | 2/1998 |
| WO | WO 98/15853 | 4/1998 |
| WO | WO 98/26312 | 6/1998 |
| WO | WO 98/35243 | 8/1998 |
| WO | WO 98/46548 | 10/1998 |
| WO | WO 99/35091 | 7/1999 |
| WO | WO 99/35516 | 7/1999 |
| WO | WO 99/48044 | 9/1999 |
| WO | WO 99/49408 | 9/1999 |
| WO | WO 99/50690 | 10/1999 |
| WO | WO 99/65002 | 12/1999 |
| WO | WO 99/67099 | 12/1999 |
| WO | WO 9965548 | 12/1999 |
| WO | WO 00/03313 | 1/2000 |
| WO | WO 00/21031 | 4/2000 |
| WO | WO 00/21032 | 4/2000 |
| WO | WP 00/21030 | 4/2000 |
| WO | WO 0025720 | 5/2000 |
| WO | WO 01/24690 | 4/2001 |
| WO | WO 01/63368 | 8/2001 |

* cited by examiner

MEDICAMENT DISPENSER

This application is filed pursuant to 35 U.S.C. §371 as a United States National Phase Application of International Application No. PCT/EP01/01941 filed 21 Feb. 2001, which claims priority from GB 0004456.0 filed 26 Feb. 2000 in the United Kingdom.

TECHNICAL FIELD

The present invention relates to a medicament dispenser, particularly an inhalation device. The medicament dispenser has a radiofrequency identifier attached thereto.

Medical dispensers are well known for the dispensing of various kinds of medicament. Inhalation devices, such as metered dose inhalers (MDIs) and dry powder inhalers are also well known for the delivery of medicament for the treatment of respiratory disorders.

The manufacture of medical dispensers requires careful control to ensure compliance with product specifications. Similarly, the packaging, distribution and sale of medical dispensers is carefully controlled to ensure consistent product quality and security for the patient. It is common practice to mark the dispenser and any packaging therefor with various codings and serial numbers for use in checking product integrity. Widely used marking techniques include printing and the use of bar codes.

In the event of a patient complaint which results in return of the medical dispenser or indeed in the event of a product recall for any other reason, the manufacturer employs the codings and serial numbers to check the product details.

Counterfeiting is known to be a problem with medical dispensers given the often high resale value of the product. Product marking is further employed to reduce the opportunities for counterfeiting and in particular, to make counterfeit products more readily identifiable.

The Applicants have now devised a method for marking a medical dispenser product of greater sophistication than presently used techniques. The method involves the use of a radiofrequency identifier having a memory structure which allows for large amounts of information to be stored thereon. The memory structure can be arranged such that parts of the memory are read-only, and may be programmed during manufacture, other parts are read/write and further parts are password protectable. Transfer of information to or from the memory is readily achievable by the use of a reader which is typically remote from the medical dispenser, thereby miminising the need for direct product handling. The reader also has the capability of writing information to the memory. In further aspects, the reader can be arranged to simultaneously read the memory of multiple radiofrequency identifiers on multiple medicament dispensers.

A principal advantage of the present invention is the ability to store many types of information in different parts of the memory structure of the radiofrequency identifier on the medical dispenser. The information is furthermore stored in a form which is readily and accurately transferable. The information could for example, include manufacturing and distribution compliance information written to the memory at various points in the manufacturing or distribution process, thereby providing a detailed and readily accessible product history of the dispenser. Such product history information may for example, be referred to in the event of a product recall. The compliance information could for example, include data and time stamps. The information could also include a unique serial number stored in encrypted form or in a password protectable part of the memory which uniquely identifies the product and therefore may assist in the detection and prevention of counterfeiting. The information could also include basic product information such as the nature of the medicament and dosing information, customer information such as the name of the intended customer, and distribution information such as the intended product destination.

PCT patent application no. WO92/17231 describes a metered dose inhaler having a microelectronic assembly thereon. The medicament container includes a set of electrically conducting strips which store information about the medicament container in digital form. The housing of the device includes electrical contact fingers which are contactable with the strips to enable reading of the information to a microelectronic memory on the housing.

SUMMARY OF INVENTION

According to the present invention there is provided a medicament dispenser comprising a housing; a medicament container; a dispensing mechanism for dispensing medicament from the medicament container; and a radiofrequency identifier, in the form of a radiofrequency identification tag comprising an antenna for transmitting or receiving radiofrequency energy and an integrated circuit chip connecting with the antenna, the radiofrequency identifier connecting to the housing or the medicament container. The dispensing mechanism may, for example, comprise a valve with/without a metering chamber for dispensing aerosol formulations of medicaments, or opening/peeling mechanisms for blister strips/packs for dispensing dry powder medicaments.

The medicament container may for example, be a bottle, vial, drum, syringe, ampoule, blister pack, sachet, cartridge, delivery device, tube, bulk sack, canistor or blister strip. The container may for example, comprise glass, metal, pastic or rubber materials. The medicament may for example, be in powder, liquid, solution, aerosol, or tablet form.

The radiofrequency identifier can be any known radiofrequency identifier. Such identifiers are sometimes known as radiofrequency transponders or radiofrequency identification (RFID) tags or labels. Suitable radiofrequency identifiers include those sold by Phillips Semiconductors of the Netherlands under the trade marks Hitag and Icode, those sold by Amtech Systems Corporation of the United States of America under the trade mark Intellitag, and those sold by Texas Instruments of the United States of America under the trade mark Tagit.

The RFID tags may be used in combination and/or Integrated with other traditional product labelling methods including visual text, machine-readable text, bar codes and dot codes.

Preferably, the antenna is capable of transmitting or receiving radiofrequency energy having a frequency of from 100 KHz to 2.5 GHz.

In one aspect, the antenna is adapted to transmit or receive radiofrequency energy having a frequency of 125 KHz.

In another aspect, the antenna is adapted to transmit or receive radiofrequency energy having a frequency of 13.56 MHz.

In a further aspect, the antenna is adapted to transmit or receive radiofrequency energy having a frequency of 2.4 GHz.

Higher frequencies are preferred because the distance between the reader/writer and the identifier may be increased.

Preferably, the radiofrequency identifier is on a carrier and the carrier is mountable on the housing or the medicament container.

In one aspect, the carrier is a flexible label. In another aspect, the carrier is a rigid disc. In a further aspect, the carrier is a rectangular block. Other shapes of carrier are also envisaged.

Preferably, the carrier is mouldable to the medicament container or housing.

Preferably, the carrier encases the radiofrequency identifier. More preferably, the carrier forms a hermetic seal for the radiofrequency identifier.

In one aspect, the carrier comprises an insulating material such as a glass material or, a paper material or an organic polymeric material such as polypropylene.

Alternatively, the carrier comprises a ferrite material.

Preferably, the integrated circuit chip has a read only memory area.

Preferably, the integrated circuit chip has a write only memory area.

Preferably, the integrated circuit chip has a read/write memory area.

Preferably, the integrated circuit chip has a one-time programmable memory area. More preferably, the one-time programmable memory area contains a unique serial number.

Preferably, the intergrated circuit chip has a preset memory area containing a factory preset, non-changeable, unique data item. The preset memory stem is most preferably in encrypted form.

Preferably, the integrated circuit chip has plural memory areas thereon.

Preferably, any memory area contains data in encrypted form. Electronic methods of checking identity, error detection (e.g. cyclic redundancy check (CRC), and data transfer may also be employed.

Preferably, any memory area is password protected.

In one preferred aspect, the integrated circuit has plural memory areas thereon including a read only memory area containing a unique serial number, which may for example be embedded at the time of manufacture; a read/write memory area which can be made read only once information has been written thereto; and a password protected memory area containing data in encrypted form which data may be of anti-counterfeiting utility.

In one aspect, the medicament container is an aerosol container. Preferably, the aerosol container comprises a suspension of a medicament in a propellant. Preferably, the propellant comprises liquefied HFA134a, HFA-227 or carbon dioxide. Alternatively, the aerosol container comprises a solution of a medicament in a solvent.

In another aspect, the medicament container is a dry-powder container. Preferably, the dry-powder container comprises medicament and optionally excipient in dry-powder form.

Preferably, the medicament is selected from the group consisting of albuterol, salmeterol, fluticasone propionate, beclomethasone dipropionate, salts or solvates thereof and any mixtures thereof.

Preferably, the housing comprises a mouthpiece for inhalation therethrough.

According to another aspect of the present invention there is provided a system for dispensing medicament comprising a medicament dispenser as hereinbefore described and a reader for reading data from the radiofrequency identifier by transmitting radiofrequency energy thereto and receiving radiofrequency energy therefrom. Preferably the reader is remote from the medicament dispenser and may, for example, be in the form of a hand-held/portable electronic device such as a personal digital assistant (PDA).

Preferably, the reader is capable of reading individual and multiple radiofrequency identifiers simultaneously by differentiating between individual radiofrequency identifiers within the same antenna field. The system thus has 'anti-collision' capability.

Preferably the reader is capable of writing data to the radiofrequency identifier by transmitting radiofrequency energy thereto.

Preferably, at least one reader additionally comprises or is in communication with an electronic data management system with input/output capability comprising a memory for storage of data; a microprocessor for performing operations on said data; and a signal output for outputting a signal relating to the data or the outcome of an operation on the data. The electronic data management system may be connected to a local computer or a networked computer system by any suitable method including a hard wired link, an infra red link or any other suitable wireless communications link.

Preferably, the system addtionally comprises a communicator for wireless communication with a gateway to a network computer system to enable transfer of data between the network computer system and the electronic data management system.

Preferably, the communicator enables two-way transfer of data between the network computer system and the electronic data management system.

Preferably, the data are communicable between the network computer system and the electronic data management system in encrypted form. All suitable methods of encryption or partial encryption are envisaged. Password protection may also be employed.

Preferably, the communicator employs radiofrequency or optical signals.

In one aspect, the communicator communicates directly with the gateway.

In another aspect, the communicator communicates with the gateway via a second communications device. Preferably, the second communications device is a telecommunications device, more preferably a cellular phone or pager. Preferably, the communicator communicates with the second communications device using spread spectrum radiofrequency signals. A suitable spread spectrum protocol is the Bluetooth (trade mark) standard which employs rapid (e.g. 1600 times a second) hopping between plural frequencies (e.g. 79 different frequencies). The protocol may further employ multiple sending of data bits (e.g. sending in triplicate) to reduce interference.

In one aspect, the network computer system comprises a public access network computer system. The internet is one suitable example of a public access network computer system, wherein the gateway can be any suitable gateway thereto including gateways managed by an internet service provider. The public access network computer system may also form part of a telecommunications system, which may itself be either a traditional copper wire system, a cellular system or an optical network.

In another aspect, the network computer system comprises a private access network computer system and the gateway is a secure gateway. The private access network system may for example, comprise an intranet or extranet which may for example, be maintained by a health service provider or medicament manufacturer. The secure gateway may for example include password protection; a firewall; and suitable encryption means.

Preferably, the communicator enables communication with a user-specific network address in the network computer system. More preferably, the user-specific network address is selected from the group consisting of a web-site address, an e-mail address and a file transfer protocol address and a data transfer protocol address.

Preferably, the system additionally comprises a data input system for user input of data to the electronic data management system. More preferably, the data input system comprises a man machine interface (MMI) preferably selected from a keypad, voice recognition interface, graphical user interface (GUI) or biometrics interface.

Preferably, the system additionally comprises a display for display of data from the electronic data management system to the user. The display may for example, comprise a screen such as an LED or LCD screen.

According to a further aspect of the present invention there is provided a data communicator for use with a medicament dispenser as hereinbefore described. The data communicator comprises a reader for the radiofrequency identifier capable of reading and writing data therefrom/to by transmitting radiofrequency energy thereto and receiving radiofrequency energy therefrom; and an electronic data management system with input/output capability comprising a memory for storage of said data; a microprocessor for performing operations on the data; and a signal output for outputting a signal relating to the data or the outcome of an operation on the data; and a communicator for communicating with a gateway to a network computer system to enable communication of the data between the network computer system and the microprocessor.

According to a still further aspect of the present invention there is provided a kit of parts comprising a data communicator as hereinbefore described and a medicament dispenser as hereinbefore described. The data communicator may for example, be mechanically coupled to the medicament dispenser by any suitable mechanical mechanism including grip mechanisms and snap-fit mechnisms. In a preferred aspect, the data communicator forms a snap-in module and the dispenser is shaped for receipt of the module.

BRIEF DESCRIPTION OF DRAWINGS

Embodiments of systems according to the invention will now be described with reference to the accompanying drawings in which.

DETAILED DESCRIPTION OF DRAWINGS

Figure 1A:
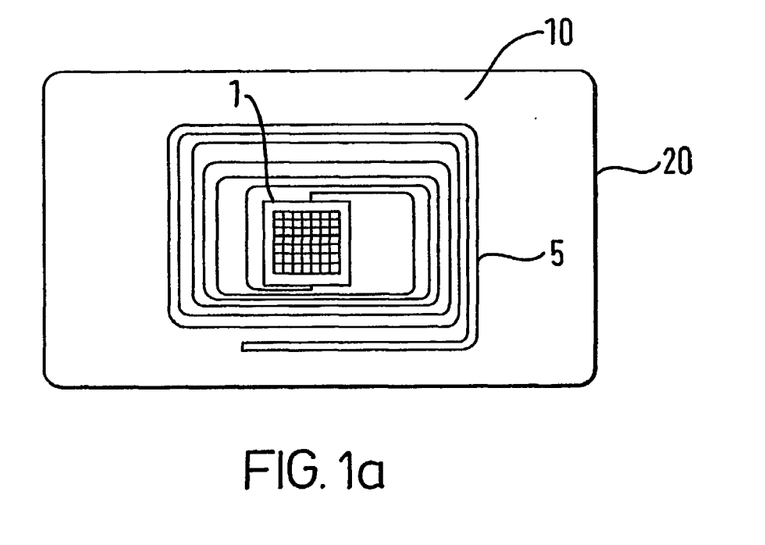
FIG. 1a is a diagram of a radiofrequency identification (RFID) tag mounted on a rectagular shaped carrier.
Figure 1B:
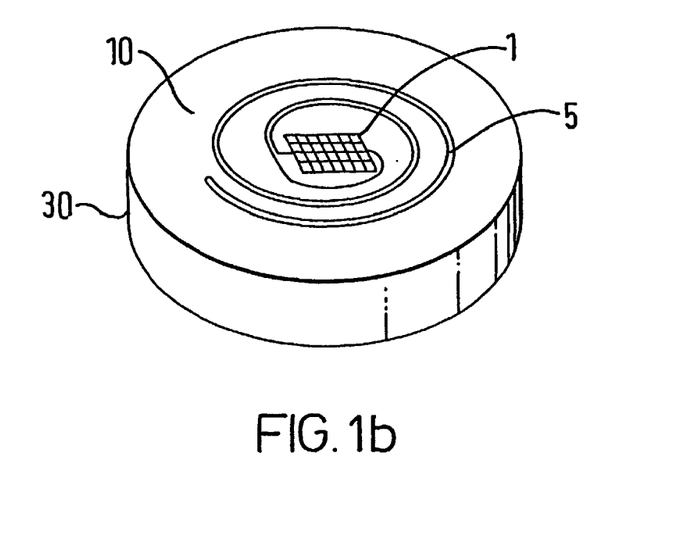
FIG. 1b is a diagram of a RFID tag mounted on a disc shaped carrier.

The basic components of an RFID tag are shown in FIGS. 1a and 1b. The tag 10 comprises a memory chip 1 which is capable of storing, transmitting and receiving information and an antenna 5. Data can be received by, or transmitted from, the chip via antenna 5 which is connected to the chip. The antenna 5, is capable of receiving or transmitting radiofrequency energy over a wide band width, ranging from 100 KHz to 2.4 GHz. The tags 10 are hermetically mounted on or sealed in a rectangular 20 (FIG. 1a) or disc 30 (FIG. 1b) shaped carrier. The carrier, which generally comprises an insulating material such as glass or ferrite based material, may take several forms such as a flexible label, as in Figure 1a, a rectangular block or a rigid disc (FIG. 1b).

Figure 2:
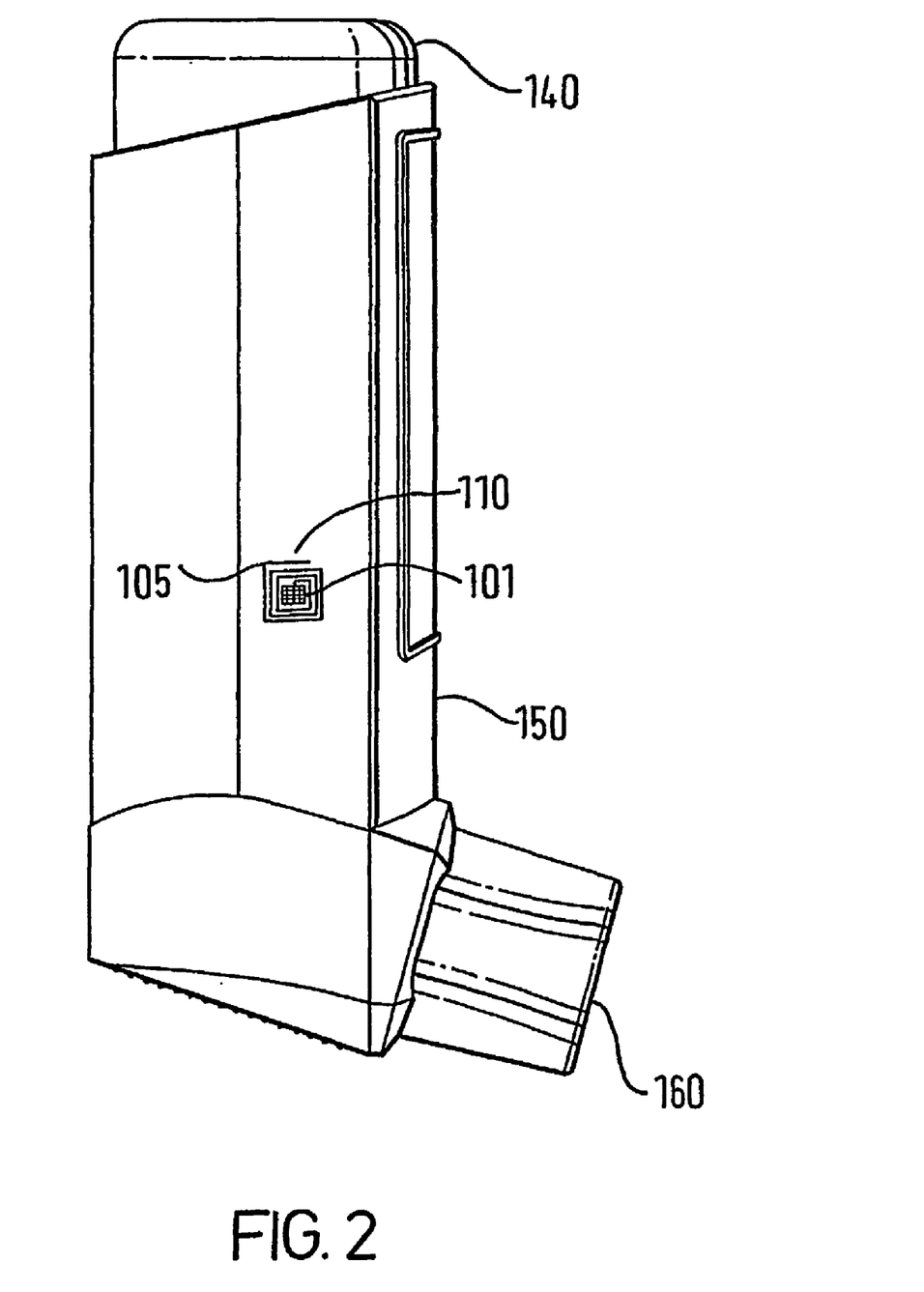
FIG. 2 is a drawing of metered dose inhaler with a RFID tag moulded to the body of the housing.

FIG. 2 shows a standard-form metered dose inhaler for the delivery of inhalable medicament comprising a tubular housing 150 in which an aerosol container 140 is located. A RFID tag 110 comprising chip 101 and antenna 105 is moulded into the body of the housing 150. The housing is open at one end and is closed at the other. A dispensing outlet 160 leads laterally from the closed end of the housing 150. In the embodiment illustrated, the outlet 160 is in the form of a mouthpiece intended for insertion into the mouth of the patient but it may, if desired, be designed as a nozzle for insertion into the patient's nostril.

Figure 3:
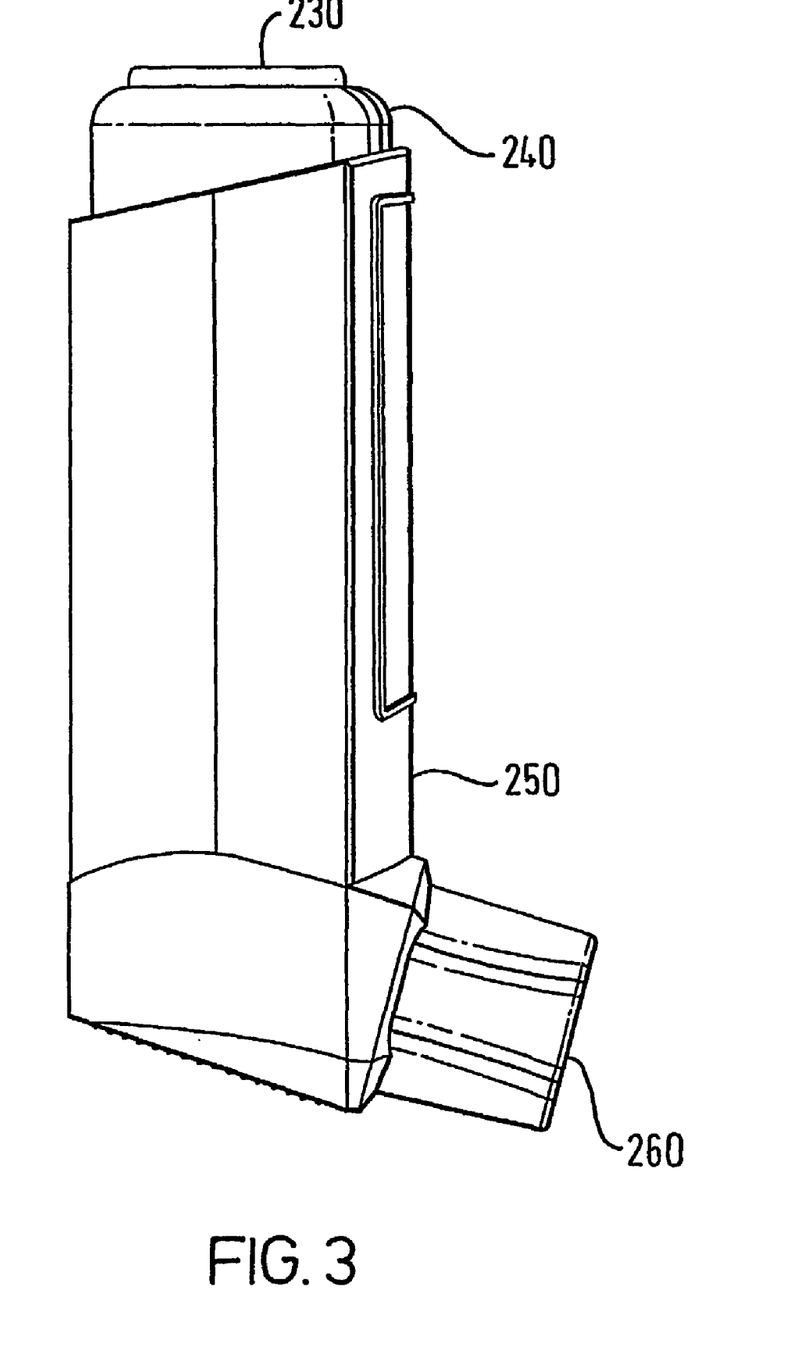
FIG. 3 is a drawing of a metered dose inhaler with a disc shaped RFID tag attached to the aerosol container.

FIG. 3 depicts another standard metered-dose inhaler, comprising housing 250, mouthpiece 260 and aerosol container 240. A RFID tag mounted on a disc shaped carrier 230 is attached to the aerosol container 240. It will be understood from both FIG. 1 and FIG. 2 that different shaped carriers may be used to affix the RFID tag to the housing, the aerosol container or the mouthpiece. Attachment of the disc shaped carrier to the aerosol container 240 may be by adhesive, hermetic or welding means.

Figure 4:
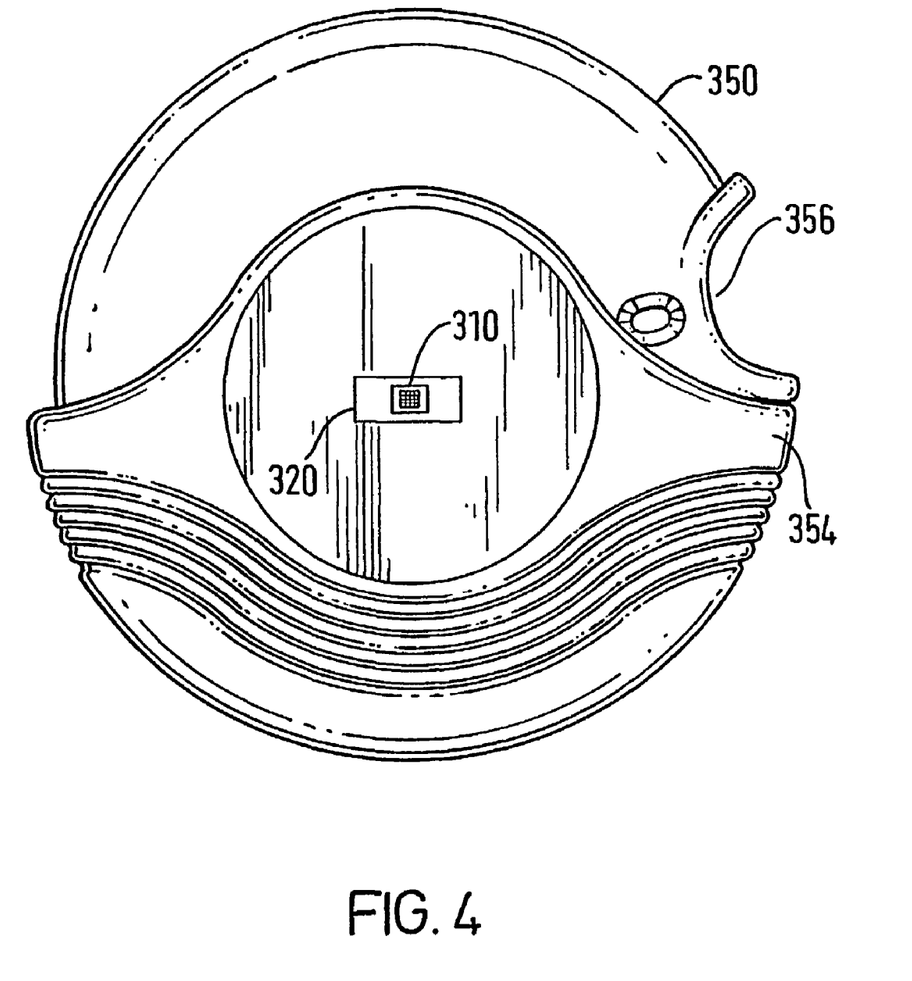
FIG. 4 is a drawing of a dry powder inhaler with a rectangular shaped RFID tag attached to the body of the housing.

FIG. 4 depicts a diagram of the Diskus™/Accuhaler™ dry powder dose dispenser comprising a housing 350, cover 354 and grip 356. In the illustration, a RFID tag 310 is attached to the cover 354 by a rectangular carrier 320 which may be affixed by adhesive or ermetic means to the inhaler. It will be understood that the tag 310 may be directly embedded within the body of the housing 350 (as depicted in FIG. 2). Alternatively, other forms of carrier bearing the tag, such as a disc shaped carrier, may be affixed to the housing.

Figure 5:
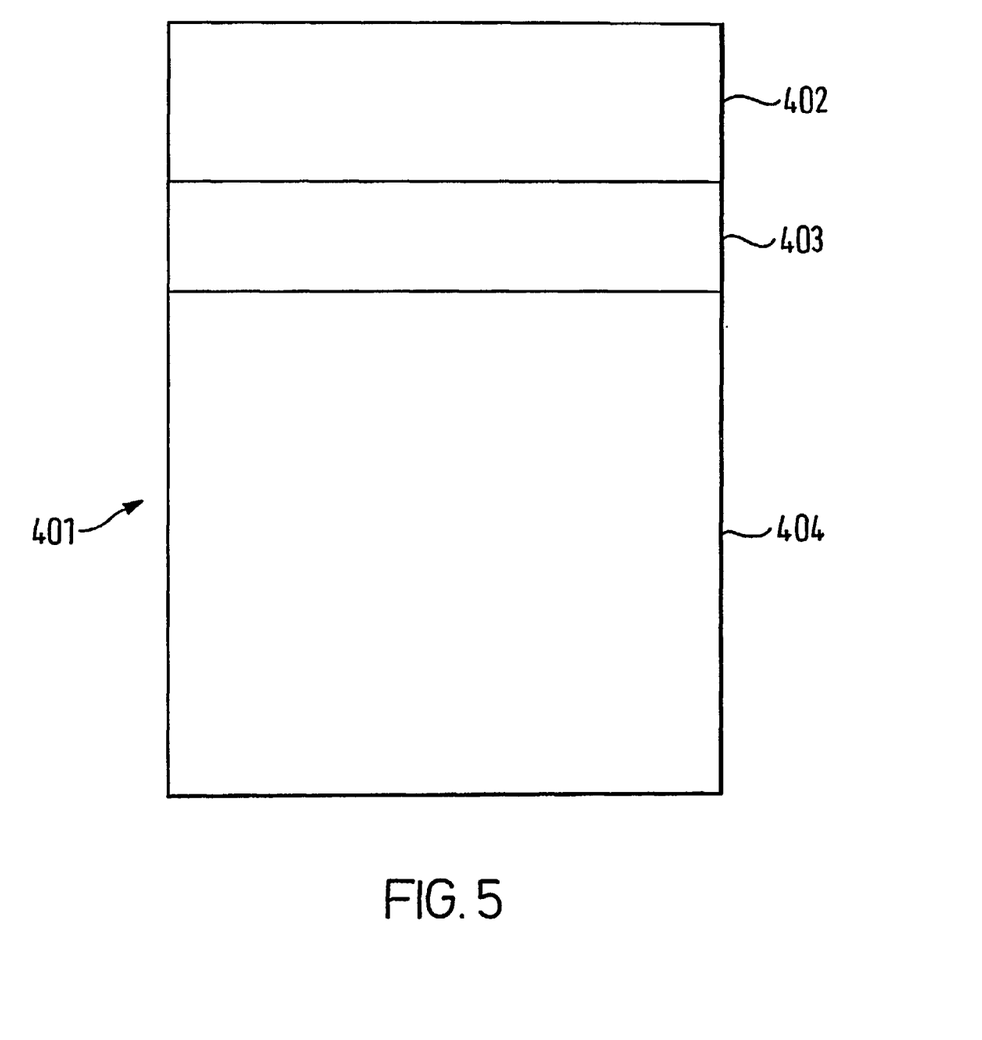
FIG. 5 is a schematic representation of the memory structure of the RFID tag.

FIG. 5 is a schematic representation of the memory structure of the RFID chip 401. Such tags are divided into unique blocks, typically numbering sixteen in total, with data being stored in non-volatile memory EEPROM, the EEPROM having a memory capacity of 512 bits with each block consisting of 4 bytes. However, for the sake of simplicity, in the illustration shown in FIG. 5 the tag is divided into three blocks 402-404 only.

The first block 402 contains unique tag identifiers such as serial numbers, this information being in a read only format and being encoded on the tag at the time of manufacture such that this information cannot be altered once set.

The second block 403 permits write access conditions to be determined for the third block 404, for example to allow read and write access to the remaining blocks. This block may be considered a 'secret area' in that access requires mutual authentication and enciphered data communications are used in this area. The second block 403 may be made read only once information has been written to it, i.e. it may become one time programmable.

The third block 404 can be considered to be a 'user' or 'public' area in that it may be programmed, by block two

403, such that information may be read from or written to it. This is generally the format in operation, information being read from and written to this area. Access can be password protected and data may be in encrypted format to enhance security.

In use, information from block one 402 (i.e. the unique serial number) will generally be used to identify the tag at each stage in a pre-determined process. Information will also be read from block three 404, to ensure that a given step in the operation has occurred. If satisfied that the operation has taken place successfully then additional information is written to block three 404, following the successful completion of the next stage in the process. Each step in the process is therefore validated and recorded by means of reading data on the chip and by transferring new information to it. These data can be stored electronically and the process monitored from a centralised work station.

Figure 6:
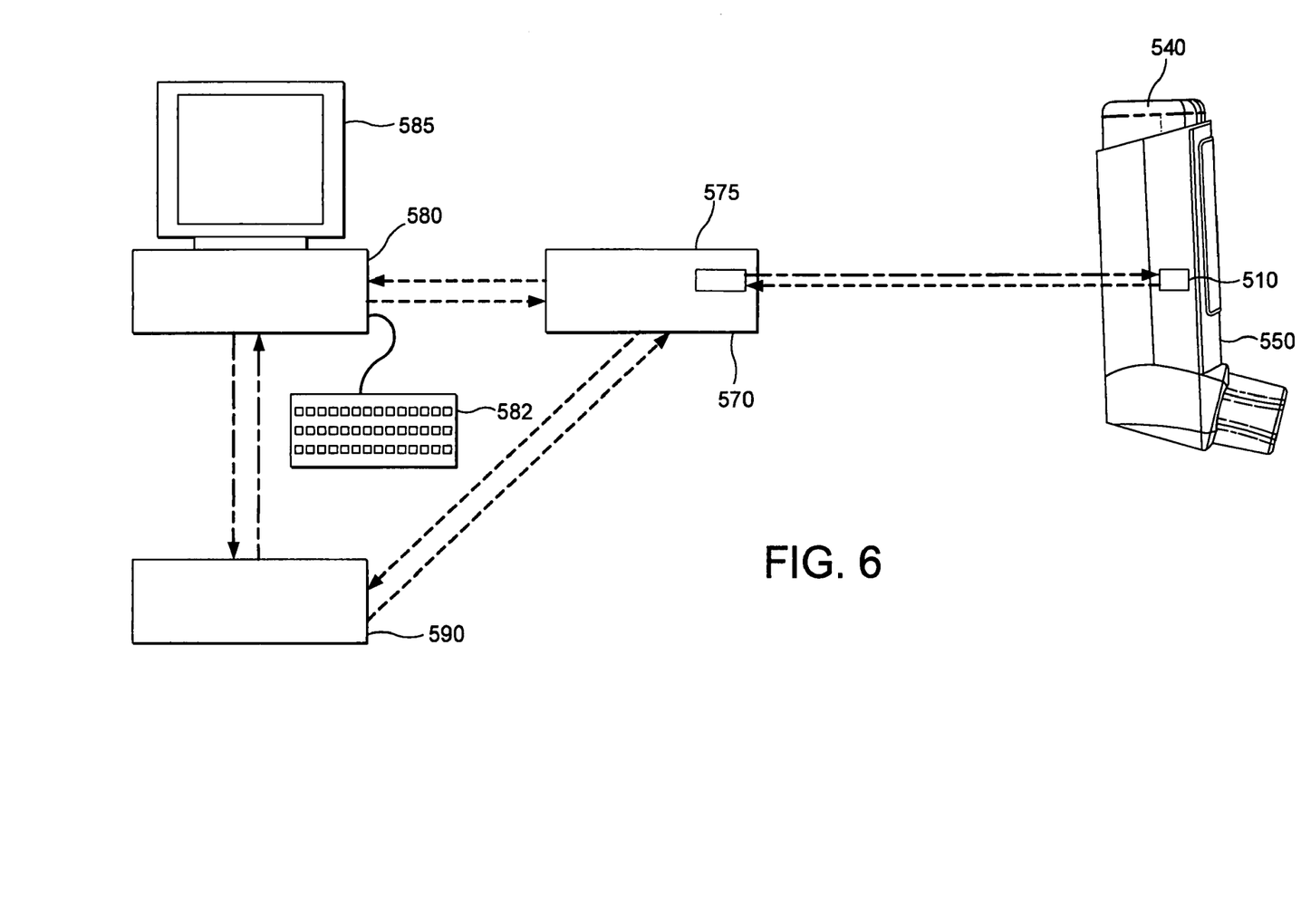
FIG. 6 is a schematic representation of a system incorporating a RFID tag, reader, PC and communications network.

FIG. 6 is a schematic representation of a system wherein RFID tags are used to monitor a process involving a medicament dispenser. The system comprises a metered dose inhaler, consisting of a housing 550 in which an aerosol container 540 is located and to which a RFID tag 510 is affixed, a reader 570 for reading data from the RFID tag 510, an electronic data management system 580 with a visual display unit 585, and a networked computer system 590. The reader 570 transmits radiofrequency energy from antenna 575 to RFID tag 510 and receives transmitted radiofrequency energy therefrom. The antenna 575 may be built into the reader 570 as illustrated or be remotely located from it, connecting to it via a jack plug.

The reader 570 reads information from tag 510 to uniquely identify the tag and validate that a particular step in a pre-determined process has occurred. The information may then pass to an electronic data management system 580 with visual display means 585, for processing and storage of the information. This information can be utilised locally or transferred to a networked computer system 590 for further processing and storage. Alternatively, data from the reader 570 may be directly transmitted to the networked computer system 590. Data transfer from the reader 570 to the local electronic data management system 580 and/or to the networked computer system 590 can be mediated by conventional electrical wiring, or by wireless means such as radio or infra red frequency energy. The networked computer system 590 and/or the local electronic data management system 580 may also transmit data to the RFID tag 510 via reader 570 by use of such means, the networked computer 590 communicating directly with reader 570 or indirectly via the data management system 580. The reader 570 then writes information to the RFID tag 510 once a specific process has been completed. User input to the local electronic data management system 580 is by means of a man-machine interface (MMI) in the form of a keyboard 582.

Figure 7:
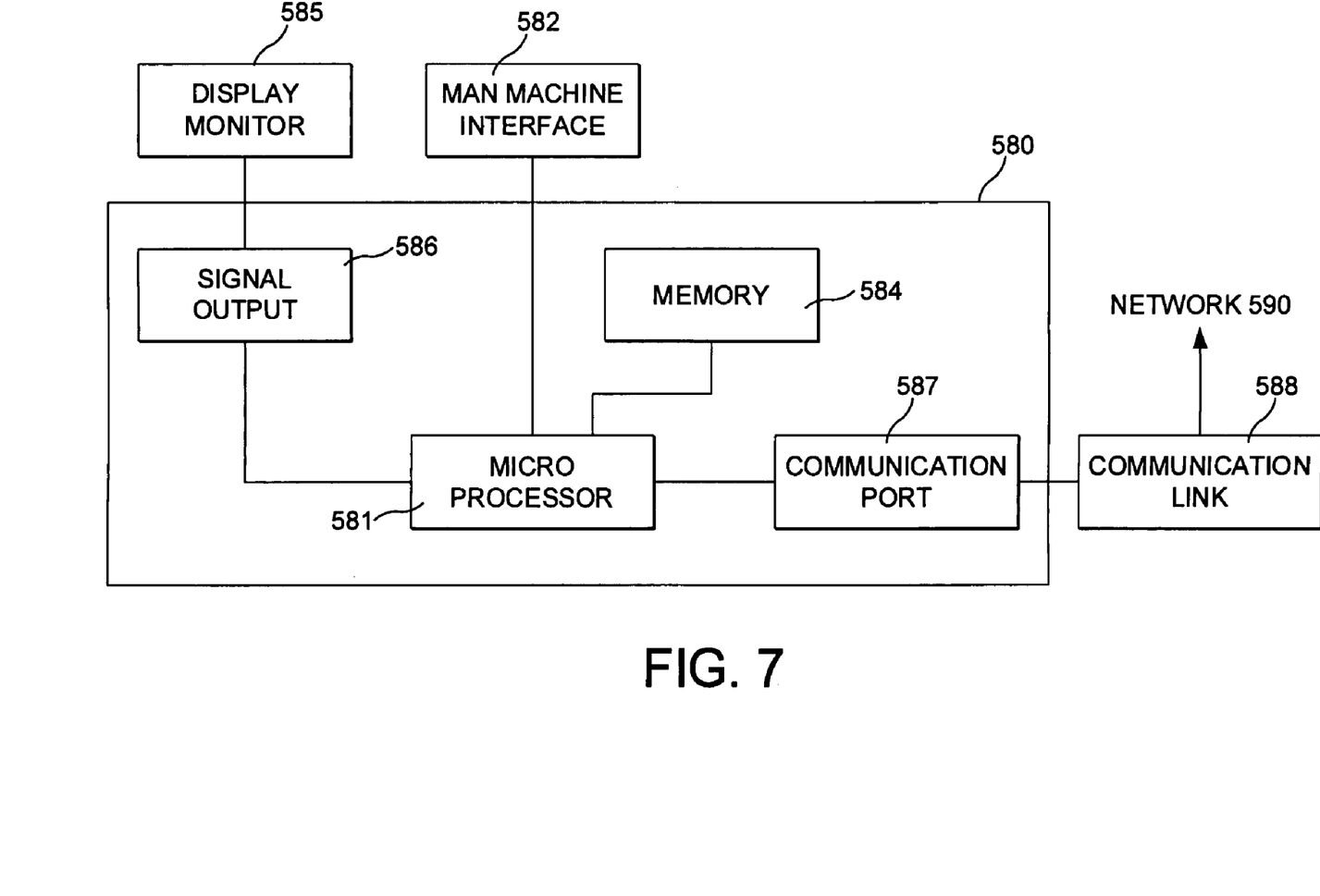
FIG. 7 is a schematic of a circuit diagram for one embodiment of the local electronic data management system of the present invention.

FIG. 7 shows a circuit diagram for the local electronic data management system 580. Central processor unit (CPU) 581 communictes with man-machine interface 582; memory 584; display monitor 585 via signal output 586; and communicator 588 via comms port 587. Communicator 588 in turn, communicates to network 590.

Whilst the present invention has been described in detail in respect of a medicament dispenser actuable manually by the patient it will be appreciated that other actuation mechanisms can be substituted. In particular, the use of a breath operated inhaler in which the actuation is assisted, and is responsive to, preferably triggered by, the inward breath of the patient, is also envisaged.

It may be appreciated that any of the parts of the medicament dispenser of the invention which contact the chemical suspension may be coated with materials such as fluoropolymer materials which reduce the tendency of chemical to adhere thereto. Suitable fluoropolymers include polytetrafluoroethylene (PTFE) and fluoroethylene propylene (FEP). Any movable parts may also have coatings applied thereto which enhance their desired movement characteristics. Frictional coatings may therefore be applied to enhance frictional contact and lubricants used to reduce frictional contact as necessary.

The medicament dispenser of the invention is in one aspect suitable for dispensing medicament, particularly for the treatment of respiratory disorders such as asthma and chronic obstructive pulmonary disease. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. s the sodium salt), ketotifen or nedocromil (e g. as the sodium salt); anti-infectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6$\alpha$, 9$\alpha$-difluoro-11$\beta$-hydroxy-16$\alpha$-methyl-3-oxo-17$\alpha$-propionyloxy-androsta-1,4-diene-17$\alpha$-carbothioic acid S-(2-$\alpha$oxo-tetrahydro-furan3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R,3R,4S,5R)-2-[6-Amino -2-(1S-hydroxymethyl-2-phenyl-ethylamino)-purin-9-yl]-5-(2-ethyl-2H-tetrazol-5-yl)-tetrahydro-furan-3,4-diol (e.g. as maleate); $\alpha$4 integrin inhibitors e.g. (2S)-3-[4-({[4-(aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant. Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (e.g. as the fumarate salt) in combination with an antiinflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt). A further combination of particular interest is budesonide and formoterol (e.g. as the fumarate salt).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

The invention claimed is:

1. An inhalation device for dispensing a medicament comprising
   a housing;
   a medicament container;
   a dispensing mechanism for dispensing medicament from the medicament container; and
   connecting to said housing or to said medicament container, a radiofrequency identifier, in the form of a passive radiofrequency identification tag comprising:
      an antenna for receiving radiofrequency energy originating from an external remote reader and returning data to said reader; and
      an integrated circuit chip connecting with said antenna.

2. An inhalation device according to claim 1, wherein the antenna is capable of receiving radiofrequency energy having a frequency of from 100 KHz to 2.5 GHz.

3. An inhalation device according to claim 2, wherein the antenna is adapted to receive radiofrequency energy having a frequency of 125 KHz.

4. An inhalation device according to claim 2, wherein the antenna is adapted to receive radiofrequency energy having a frequency of 13.56 MHz.

5. An inhalation device according to claim 2, wherein the antenna is adapted to receive radiofrequency energy having a frequency of 2.4 GHz.

6. An inhalation device according to claim 1, wherein the radiofrequency identifier is on a carrier and the carrier is mountable on the housing or the medicament container.

7. An inhalation device according to claim 6, wherein the carrier is a flexible label.

8. An inhalation device according to claim 6, wherein the carrier is a rigid disc.

9. An inhalation device according to claim 6, wherein the carrier is a rectangular block.

10. An inhalation device according to claim 6, wherein the carrier is mouldable to the medicament container or housing.

11. An inhalation device according to claim 6, wherein the carrier encases the radiofrequency identifier.

12. An inhalation device according to claim 11, wherein the carrier forms a hermetic seal for the radiofrequency identifier.

13. An inhalation device according to claim 6, wherein the carrier comprises an insulating material.

14. An inhalation device according to claim 13, wherein the insulating material comprises a glass material, paper material or organic polymeric material.

15. An inhalation device according to claim 13, wherein the carrier comprises a ferrite material.

16. An inhalation device according to claim 1, wherein the integrated circuit chip has a read only memory area.

17. An inhalation device according to claim 16, wherein the integrated circuit chip has plural memory areas thereon.

18. An inhalation device according to claim 16, wherein said integrated circuit chip comprises memory containing data in encrypted form.

19. An inhalation device according to claim 1, wherein the integrated circuit chip has a write only memory area.

20. An inhalation device according to claim 1, wherein the integrated circuit chip has a read/write memory area.

21. An inhalation device according to claim 1, wherein the integrated circuit chip has a one-time programmable memory area.

22. An inhalation device according to claim 21, wherein the one time programmable memory area contains a unique serial number.

23. An inhalation device according to claim 1, wherein the integrated circuit chip has a preset memory area containing a non-changeable data item.

24. An inhalation device according to claim 1, wherein said integrated circuit chip comprises a memory area and said memory area is password protected.

25. An inhalation device according to claim 1,
    wherein the integrated circuit chip has plural memory areas thereon including
    (a) a read only memory area containing a unique serial number;
    (b) a read/write memory area which can be made read only; and
    (c) a password protected memory area containing data in encrypted form.

26. An inhalation device according to claim 1, wherein said medicament container is an aerosol container.

27. An inhalation device according to claim 26, wherein said aerosol container comprises a suspension of a medicament in a propellant.

28. An inhalation device according to claim 27, wherein, said propellant comprises liquefied hydrofluoroalkane ("HFA") 134a, HFA-227 or carbon dioxide.

29. An inhalation device according to claim 28, wherein said aerosol container comprises a solution of a medicament in a solvent.

30. An inhalation device according to claim 27, wherein the medicament is selected from the group consisting of albuterol, salmeterol, fluticasone propionate, beclomethasone dipropionate, salts or solvates thereof and any mixtures thereof.

31. An inhalation device according to claim 1, wherein said medicament container is a dry-powder container.

32. An inhalation device according to claim 31, wherein said dry-powder container comprises medicament and optionally excipient in dry-powder form.

33. An inhalation device according to claim 1, wherein the housing comprises a mouthpiece for inhalation of medicament from the medicament container therethrough.

34. A system for dispensing medicament comprising an inhalation device according to claim 1; and
    a remote external reader for reading data from the radiofrequency identifier by transmitting radiofrequency energy thereto and receiving data therefrom.

35. A system according to claim 34 wherein said reader is capable of reading individual and multiple radiofrequency identifiers simultaneously by differentiating between individual radiofrequency identifiers within the same antenna field.

36. A system according to claim 34, wherein said reader additionally comprises an electronic data management system with input/output capability comprising
a memory for storage of data;
a microprocessor for performing operations on said data; and
a signal output for outputting a signal relating to the data or the outcome of an operation on the data.

37. A system according to claim 36, additionally comprising a communicator for wireless communication with a gateway to a network computer system to enable transfer of data between the network computer system and the electronic data management system.

38. A system according to claim 37, wherein the communicator enables two-way transfer of data between the network computer system and the electronic data management system.

39. A system according to claim 37, wherein the data are communicable between the network computer system and the electronic data management system in encrypted form.

40. A system according to claim 37, wherein the communicator communicates directly with the gateway.

41. A system according to claim 37, wherein the network computer system comprises a public access network computer system.

42. A system according to claim 37, wherein the network computer system comprises a private access network computer system and the gateway is a secure gateway.

43. A system according to claim 37, wherein the communicator enables communication with a user-specific network address in the network computer system.

44. A system according to claim 43, wherein the user-specific network address is selected from the group consisting of a web-site address, an e-mail address, a file transfer protocol address and a data transfer protocol address.

45. A system according to claim 37, additionally comprising a data input system for user input of data to the electronic data management system.

46. A system according to claim 45, wherein said data input system comprises a man machine interface (MMI).

47. A system according to claim 36, additionally comprising a display for display of data from the electronic data management system to the user.

48. An inhalation device according to claim 1, wherein the integrated circuit chip has a memory area containing data indicating that a predetermined process step relating to the dispenser inhalation device has occurred.

49. An inhalation device according to claim 48, wherein the pre-determined process step is a manufacturing and/or distribution process step of the inhalation device.

50. An inhalation device according to claim 49, wherein the data indicating that a pre-determined process step relating to the inhalation device has occurred is written to the memory during the manufacturing and/or distribution process.

51. An inhalation device according to claim 50, wherein the data indicating that a pre-determined process step relating to the inhalation device has occurred comprises a time stamp.

* * * * *